United States Patent [19]

Whitehouse et al.

[11] Patent Number: 4,743,265
[45] Date of Patent: May 10, 1988

[54] ARTICULATED CATHETER PLACEMENT DEVICE

[75] Inventors: Craig M. Whitehouse, Branford; Allan Burt, East Haven; Clement M. Catalano, Jr., Clinton, all of Conn.

[73] Assignee: DIJ Catheter Corp, Branford, Conn.

[21] Appl. No.: 855,524

[22] Filed: Apr. 23, 1986

[51] Int. Cl.⁴ .............................................. A61M 5/00
[52] U.S. Cl. ................................................... 604/161
[58] Field of Search ............................... 604/158–163, 604/51–53

[56] References Cited

U.S. PATENT DOCUMENTS

| | | | |
|---|---|---|---|
| 3,185,152 | 5/1965 | Ring | 128/214 |
| 3,330,278 | 7/1967 | Santomieri | 128/214.4 |
| 3,359,978 | 12/1967 | Smith, Jr. | 128/214.4 |
| 3,382,872 | 5/1968 | Rubin | 604/161 |
| 3,545,443 | 12/1970 | Ansari | 128/347 |
| 3,550,591 | 12/1970 | MacGregor | 128/214.4 |
| 3,592,193 | 7/1971 | Huggins | 128/214.4 |
| 3,596,658 | 8/1971 | Lange et al. | 128/214.4 |
| 3,598,118 | 8/1971 | Warren | 128/214.4 |
| 3,651,807 | 3/1972 | Huggins | 604/161 |
| 3,677,243 | 7/1972 | Nerz | 128/214.4 |
| 4,166,469 | 9/1979 | Littleford | 128/784 |
| 4,177,809 | 12/1979 | Moorehead | 128/214.4 |
| 4,300,553 | 11/1981 | Seberg | 128/214.4 |
| 4,306,562 | 12/1981 | Osborne | 128/348 |
| 4,377,165 | 3/1983 | Luther et al. | 128/214.4 |
| 4,401,433 | 8/1983 | Luther | 604/159 |
| 4,412,832 | 11/1983 | Kling et al. | 604/164 |
| 4,449,973 | 5/1984 | Luther | 604/161 |
| 4,471,778 | 9/1984 | Toye | 604/160 X |

Primary Examiner—Dalton L. Truluck
Attorney, Agent, or Firm—Workman, Nydegger & Jensen

[57] ABSTRACT

A device for placing a catheter in a patient comprises a splittable hollow needle having a bifurcated proximal end and a pair of handles, each having a body portion and an extension, which are attached to a respective bifurcation of the hollow needle. With each handle attached to a respective bifurcation, the body portions of the handles are juxtaposed and the catheter is slidably received within the hollow needle. A squeezing together of the extensions will cause the body portions to separate and spread the bifurcations to split the needle. The splitting of the needle permits disjoining the needle from the catheter.

21 Claims, 5 Drawing Sheets

ARTICULATED CATHETER PLACEMENT DEVICE

BACKGROUND OF THE INVENTION

This invention relates generally to catheter placement devices. More particularly, this invention relates to a device which provides for a hollow needle or cannula in surrounding relationship to a catheter and the means for splitting the needle to separate the needle from the catheter. This invention is particularly, though not exclusively, useful for the intravenous or subcutaneous placement of a catheter.

DESCRIPTION OF THE PRIOR ART

Numerous medical procedures require the placement of a catheter in a patient. In each procedure the positioning of the catheter is accomplished for a specific purpose with particular therapeutic or medical concerns in mind. Obviously, each procedure has its own requirements. In some procedures it may be desirable, and perhaps even preferable, if the patient can accomplish catheter placement by himself. In some procedures it may be necessary for the catheter to be left in place for extended periods of time. Further, in some procedures it may be very advantageous if the catheter can be placed using only one hand. Always, of course, it is necessary to ensure that the catheter placement and any extended indwelling is accomplished without compromising the sterility of either the catheter or its connection with the fluid source. Also, it is frequently desirable to have the catheter's hub or injection site somewhat distanced from the injection site to allow for greater flexibility in attaching medical devices to the catheter and to obviate the need for frequent catheter changes.

Presently, several catheter placement devices have been suggested which can be generally grouped into three separate categories. In the first category are the over-the-catheter type placement devices. These devices generally consist of a hollow needle or cannula. With this type device, the needle establishes the venapuncture or other access to the patient and the catheter, which may be either prepositioned within the needle or subsequently threaded through it, is then positioned according to the particular medical procedure being followed. Once the catheter is in place, the needle is withdrawn from the patient and separated from the catheter. The second category includes devices of the type which use a stylet inside the catheter to provide stiffness while the catheter is being positioned. With devices in this category, once the catheter is in place, the stylet is withdrawn and a patent catheter remains for use as needed. The third category, which is really a combination of the first two, includes devices that employ a hollow needle or cannula with a catheter-stylet combination inserted therethrough. With devices in the third category, initial access into the vein is accomplished by the hollow cannula and the stylet-stiffened catheter can then be threaded through the vein and into position as required.

In those procedures where a hollow cannula needle is used, there is always the problem of removing the cannula once the catheter has been properly placed. It is widely recognized that removal of the cannula is necessary in order to provide for easier operation and to reduce the possibility of infection. Several methods have been suggested for removing hollow needles or cannulae from their surrounding relationship with a catheter. As suggested in U.S. Pat. No. 3,596,658 to Lange et al., a splittable needle is provided with a longitudinally scored line which can be broken to separate the needle from the catheter once the catheter has been placed and the needle has been withdrawn from the patient. Another type of catheter placement device proposes a tear-apart cannula which is made of a material that can be separated longitudinally. Such a device is disclosed in U.S. Pat. No. 4,306,562 to Osborne. Still another version of a catheter placement device is disclosed in U.S. Pat. No. 3,382,872 to Rubin. In this version, a splittable needle is provided with handles attached to its proximal end that allow for manipulation and grasping of the cannula to assist in splitting the cannula. These devices, however, require extraordinary manipulation of the hollow needle after its withdrawal from the patient in order to split the needle and separate it from the catheter.

Where hollow needles or cannulae are used, there is a need for a catheter placement device which conveniently affects the separation of a hollow cannula or hollow needle from its surrounding engagement with a catheter. There is also the need for a catheter placement device that can be controlled and operated by a single-handed manipulation. Further, there is a need for a device which splits the needle without damaging the skin at the point where the device has been inserted into the patient. Also, there is a need for a device which can effectively set catheters in place which are very flexible and have outer diameters as small as 0.015 inches. Further, there is a need for such a device which can place these very small catheters without using a stylet.

Accordingly, it is an object of the present invention to provide a catheter placement device which can be completely controlled and operated by either hand alone. It is yet another object of the present invention to provide a catheter placement device which permits separation and removal of the positioning needle from the catheter without damage to the patient's skin at the point of insertion. It is yet another object of the present invention to provide a catheter placement device which allows the introduction of a catheter into the patient either with or without the use of a stylet. It is still another object of the present invention to provide a catheter placement device which is efficacious in placing very small catheters having very little axial strength. Yet another object of the present invention is to provide a catheter placement assembly which will predictably split the hollow needle which is used to position the catheter. It is also an object of the present invention to provide a device which is cost effective and easily manufactured.

SUMMARY OF THE INVENTION

A preferred embodiment of the novel catheter placement device comprises a slittable hollow needle which is adapted to receive a catheter therein. The hollow needle is split at its proximal end to establish a first and a second bifurcation. The device further comprises two handles, each having a body portion and an extension from the body portion. Each bifurcation is respectively attached to a handle at the end opposite from its extension and the handles are juxtaposed to bring their body portions into contact. A base member is also provided which comprises taping wings, an arch and a housing. The arch and housing are positioned on the taping wings with an opening therebetween and are aligned so that a channel extends through both of them. The hollow needle, when joined with the handles, is positioned under the arch on the base member to establish an extension of the channel extending from the base member. A catheter can then be threaded through the channel and on through the hollow needle. In accordance with the present invention, the catheter may be fixedly attached to the housing to provide additional stability for the catheter. Once the catheter is properly placed, a pinching together of the extensions causes a retraction of the needle through the arch and a spreading of the bifurcations at the opening to cause separation of the needle at the point between the arch and the housing. Since the forces required to separate the needle are generated against the base member, needle separation is accomplished without causing trauma to the skin at the insertion site. In an alternate embodiment, the base member may be eliminated.

In one variation of the novel catheter placement device, the handles of the device are provided with an intermediate flat that is formed between the body portion and the extension. The affect of the intermediate flat is to allow for a double detent operation of the handles. With this variation, the juxtaposition of the intermediate flats on the respective handles causes a first separation of the body portions that results in an initial splitting of the needle. Further movement of the handles brings the extensions into juxtaposition and causes both a spreading of the intermediate flats and a second spreading of the body portions to further split the hollow needle and disengage it from the catheter. The novel features of this invention as well as the invention itself, both as to its structure and its operation, will be best understood from the accompanying drawings taken in conjunction with the accompanying description in which similar reference characters refer to similar parts and in which:

DESCRIPTION OF THE PREFERRED EMBODIMENTS

Figure 1:
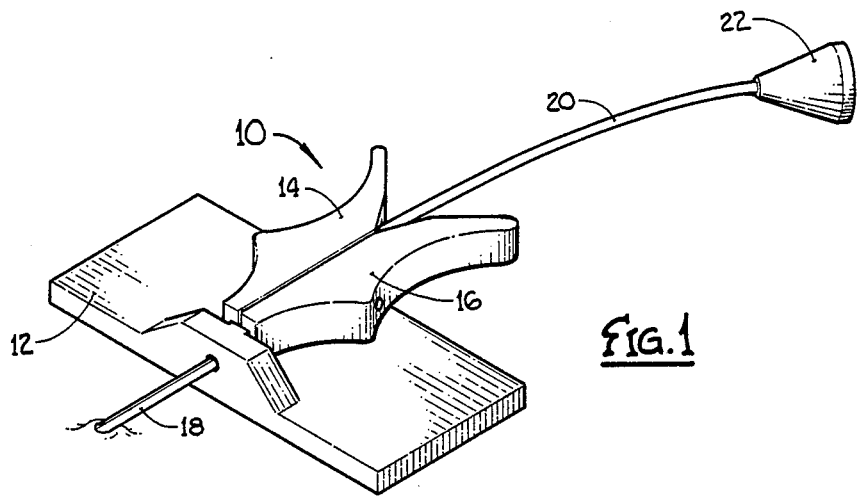
FIG. 1 is a view of the device inserted into a patient.
Figure 2:
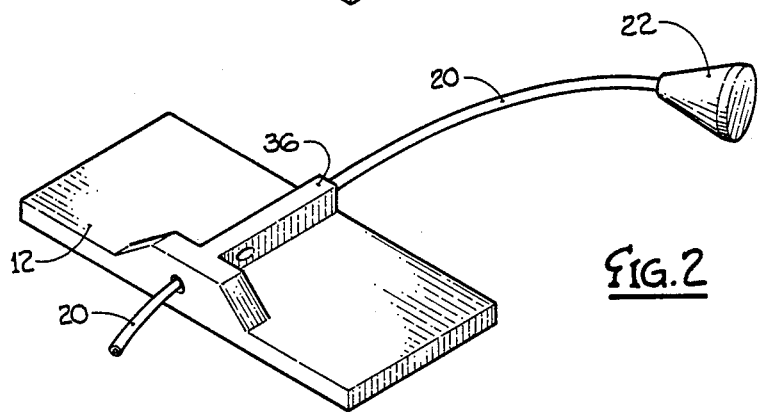
FIG. 2 is a view of the catheter and base member associated with the patient.

In FIG. 1 an embodiment of the catheter placement device of the present invention, generally designated 10, is shown immediately after its insertion into a patient. In this embodiment, the device 10 comprises a handle 14 juxtaposed against a handle 16. Both handles 14 and 16 are operatively connected with a splittable needle 18 and mounted on a base member 12. FIG. 2 shows a catheter 20 in position and stabilized by base member 12 after manipulation of device 10 has retracted splittable needle 18 from the patient and separated the splittable needle 18 from catheter 20.

Figure 3:
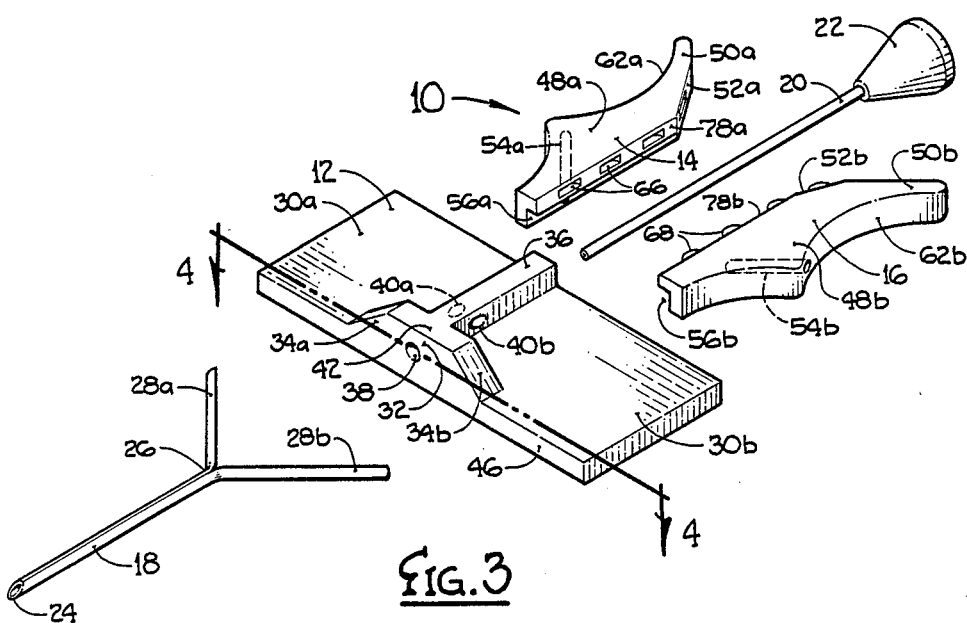
FIG. 3 is an exploded perspective view of the device.

The details of the present invention can be best appreciated by reference to FIG. 3 in which the various components of the device 10 are shown in exploded perspective. As shown in FIG. 3, device 10 incorporates a splittable needle 18 having a pointed distal end 24 and a bifurcated proximal end 26. Splittable needle 18 is hollow and adaptable to slidably receive catheter 20 therein. Preferably, hollow needle 18 is of a type as disclosed in U.S. Pat. No. 4,449,973 to Luther and manufactured by Luther Medical Products, Inc., 1940 E. Occidental St., Santa Ana, Calif. 92705. The proximal end 26 of splittable needle 18 is divided, as shown, to form a bifurcation 28a and a bifurcation 28b.

Device 10 also comprises a handle 14 and a handle 16. The handle 14 is formed with a body portion 48a and an extension 50a which is angled from body portion 48a to form a finger grip 62a. A series of indentations 66 are formed along an edge 78a of handle 14 in a manner as shown in FIG. 3. Also, formed along the underneath side of the edge 78a of handle 14 is a recess 56a. Shown in phantom on handle 14 in FIG. 3 is an attachment slot 54a which is adapted to fixedly receive bifurcation 28a of splittable needle 18. In many important respects, handle 16 is a mirror image of handle 14. As shown in FIG. 3, the handle 16 comprises a body portion 48b having an extension 50b angled therefrom to form a finger grip 62b. Formed on handle 16 along the underneath portion of edge 78b is a recess 56b. An attachment slot 54b, similar to slot 54a, is formed on the underside of handle 16. Handle 16 is fixedly attached to bifurcation 28b of needle 18 along the attachment slot 54b of handle 16 in a manner similar to the attachment of handle 14 to bifurcation 28a of needle 18. Also, formed along edge 78b of handle 16 are a series of protuberances 68. It will be understood by the skilled artisan that, upon juxtaposition of handles 14 and 16, the protuberances 68 are received within the indentations 66 to provide both longitudinal and rotational stability for the combination. Also shown on handle 14 and handle 16 are respective intermediate flats 52a and 52b.

Still referring to FIG. 3, it can be seen that device 10 also comprises a base member 12 having oppositely disposed taping wings 30a and 30b. As envisioned by the present invention, the taping wings 30a and 30b can be provided with a suitable adhesive along the undersurface 46 of base member 12 for the purpose of securing base member 12 to the body of a patient in a manner as shown in FIG. 1 and FIG. 2. A housing 36 is formed on base member 12 as shown in FIG. 3. Also formed on base member 12 and aligned substantially perpendicular to the housing 36 is an arch 32 having reinforcing ridges 34a and 34b extending therefrom which are joined to respective taping wings 30a and 30b to provide additional rigidity for arch 32.

Figure 4A:
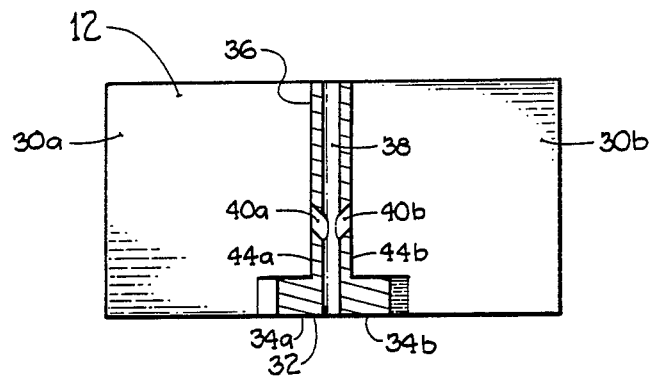
FIG. 4A is a top cross-sectional view of the base member of the device as seen along the line 4—4 in FIG. 3.

By comparing base member 12 as shown in FIG. 3 with the cross section of base member 12 as shown in FIG. 4A, it will be appreciated that housing 36 is formed with a channel 38 extending therethrough. Further, as shown in FIG. 4A, channel 38 extends through arch 32. Reinforcing ridges 34a and 34b are positioned to provide stability to the base member 12 during the taping of base member 12 to a patient and during the withdrawal of needle 18 from the patient. As clearly shown in FIG. 4A, channel 38 has oppositely disposed side openings 40a and 40b which are formed between arch 32 and housing 36 and which establish the abutments 44a and 44b. A bridge 42, as shown in FIG. 3, lies atop the openings 40a and 40b. With this structure access to channel 38 is obtained through either end of the channel 38 or through the side openings 40a and 40b.

Figure 4B:
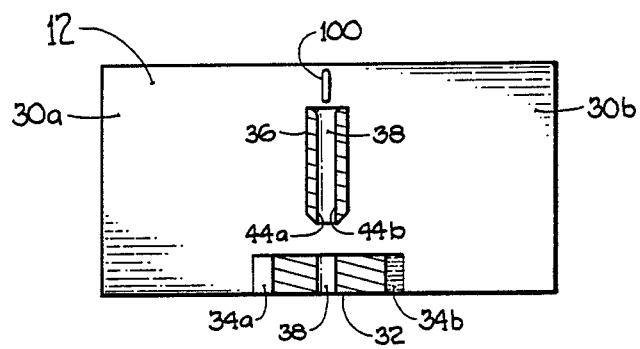
FIG. 4B is a top cross-sectional view of an alternate embodiment of the base member shown in FIG. 4A.

FIG. 4B shows an alternate embodiment for the base 12 in which the bridge 42 is removed. Like the embodiment shown in FIG. 4A, the channel 38 extends through both housing 36 and arch 32 in this alternate embodiment. Further, although bridge 42 has been removed from the alternate embodiment of FIG. 4B, the abutments 44a and 44b remain and, as will become apparent, the abutments 44a and 44b serve the same purpose as they do for the embodiment of FIG. 4A. Also shown in FIG. 4B is a cleat 100 which is formed onto base member 12 to grip and stationarily hold catheter 20 in a manner well known to the skilled artisan during the use of device 10.

The total assembly of the device 10 will be best appreciated with reference back to FIG. 3. When assembled the proximal end 26 of needle 18 is positioned within channel 38 in arch 32, and bifurcations 28a and 28b are extended respectively through the side openings 40a and 40b. The handle 14 is fixedly attached to bifurcation 28a along its attachment slot 54a in any manner well known in the art. Likewise, handle 16 is attached to bifurcation 28b of needle 18 along its attachment slot 54b. When handles 14 and 16 are attached to their respective bifurcations 28a and 28b, handle 14 is positioned against handle 16 with the body portions 48a and 48b in a side-by-side relationship. In the embodiment shown in FIG. 3, this juxtaposition causes the appropriate protuberances 68 to nest within their respective indentations 66. Further, when needle 18 is attached to the handles 14 and 16, both handle 14 and handle 16 are positioned in surrounding relationship to the housing 36 with the respective recesses 56a and 56b positioned against housing 36. This presents device 10 in the configuration shown in FIG. 1. It will be appreciated that in such a configuration, catheter 20 can be positioned within the channel 38 and extended into the hollow needle 18.

Figure 6A:
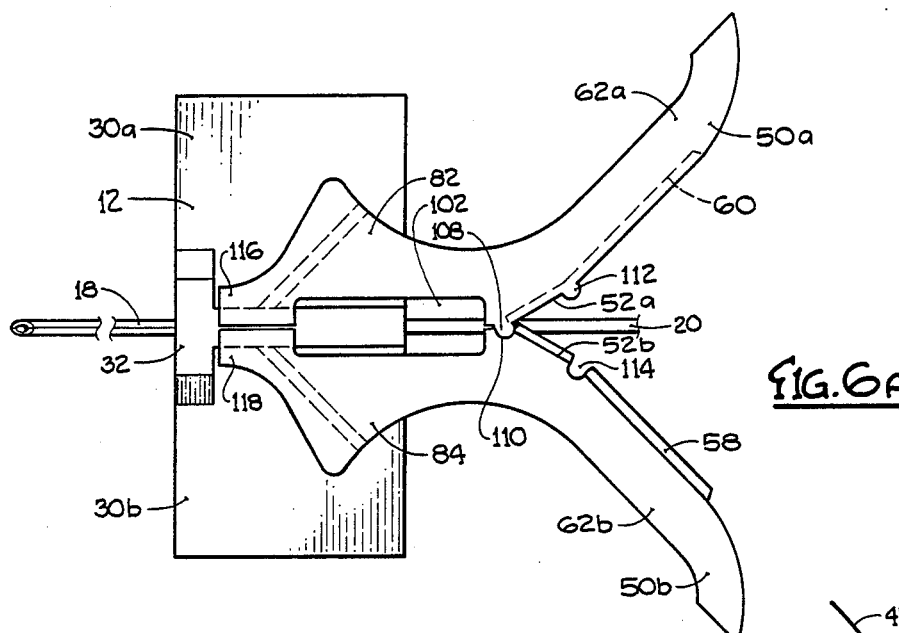
FIG. 6A is a view of the preferred embodiment of the handles of the device employing a hinged connection.
Figure 6B:
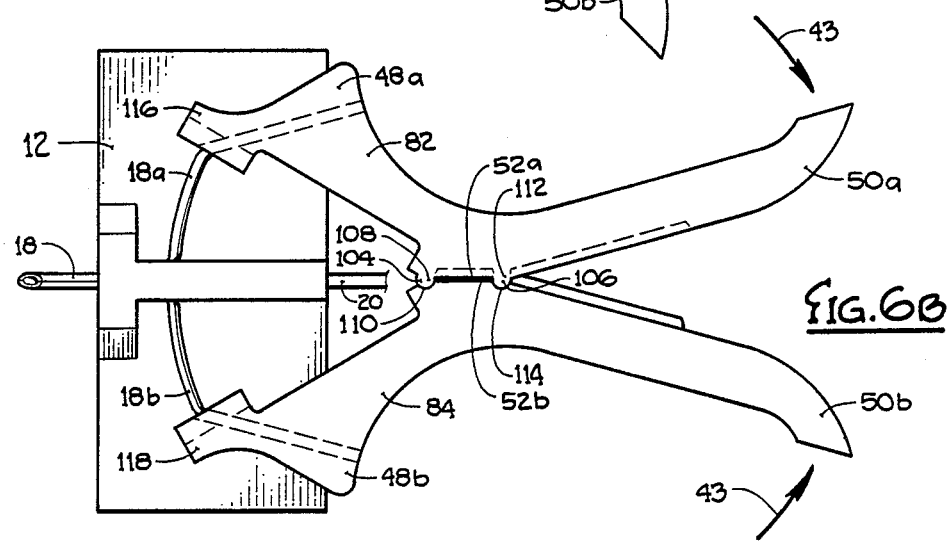
FIG. 6B is a view of the handles in FIG. 6A showing first stage separation of the handles.
Figure 6C:
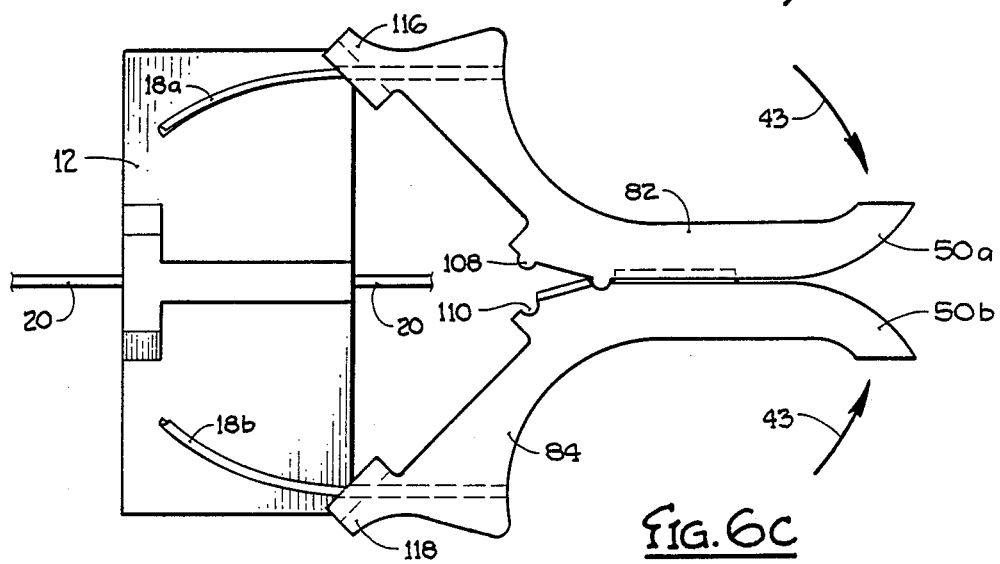
FIG. 6C is a view of the handles in FIG. 6B showing second stage separation of the handles.

Preferably, the handles of device 10 are formed as shown in FIGS. 6A, 6B and 6C so device 10 may be used with or without base member 12. For this alternating use, handles 82 and 84 may be shaped to form a hollow 102 as shown. This will facilitate the manipulation of catheter 20 as it is axially positioned within needle 18 when handles 82 and 84 are used without base member 12 or are removed therefrom. Specifically, hollow 102 allows insertion of catheter 20 further into the vein of a patient after placement of needle 18.

For its cooperation with device 10, catheter 20 may be as long as desired and extend proximally from device 10 without affecting its structure or operation. Further, it will be appreciated by the skilled artisan that the catheter 20 may be rigidly attached to the housing 36 by any means known in the art for the purpose of providing additional stability to the catheter 20 during both its placement and indwelling in the patient. As shown in FIG. 3, catheter 20 may have an entry site 22 attached to its proximal end. Entry site 22 may be any of several types, depending upon the particular needs of the medical procedure to be used, and may include a luer lock or septum fitting.

The embodiment of catheter placement device 10 like the one shown in FIG. 3, in which base member 12 is used, is particularly suitable for subcutaneous applications. For such an application, the combination of elements shown in FIG. 3 presents a unitary device which is adapted for a one-handed operation that may be accomplished by the patient himself. With this embodiment of device 10, once insertion of needle 18 into the patient is accomplished, the undersurface 46 of base member 12 can be adhesively positioned against the body of the patient. The handles 14 and 16 of device 10 may then be manipulated to withdraw hollow splittable needle 18 from the patient and split needle 18 to disjoin it from catheter 20. This operation leaves catheter 20 in place as shown in FIG. 2.

Figure 5:
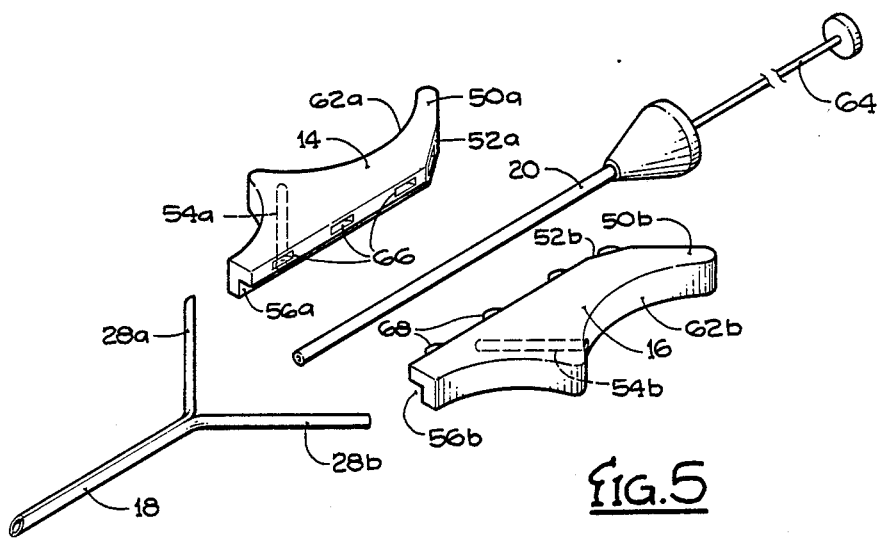
FIG. 5 is an exploded perspective view of an alternate embodiment of the device.

Referring now to FIG. 5, another embodiment of the present invention is presented which may be more suitable for procedures such as intravenous placement of catheters. It will be seen that in all important respects this alternate embodiment is the same as the preferred embodiment with the exception that base member 12 is no longer used. According to the embodiment shown in FIG. 5, handles 14 and 16 are attached respectively to bifurcations 28a and 28b as discussed above and juxtaposed with protuberances 68 nesting in the respective indentation 66. Here, the catheter 20 is positioned to lie within the area created by the side-by-side relationship of recess 56a and 56b. As will be appreciated by the skilled artisan, a stylet 64 may be used to stiffen catheter 20. Such a combination is easily adapted for use with device 10 when base member 12 is not used.

Like the embodiment just discussed, the embodiment shown in FIGS. 6A, 6B and 6C is particularly well suited for intravenous placement of catheters. An additional advantage is obtained, however, since hollow 102 formed between handles 82 and 84, as previously discussed, permits easy manipulation of catheter 20 while it is still associated with device 10. The embodiment for handles 82 and 84 shown in FIGS. 6A, 6B and 6C also includes hinges 104 and 106 which are respectively created by the interaction of finger 108 with recess 110 and finger 112 with recess 114 to add stability to the combination during its manipulation. Further, it will be seen in FIGS. 6A, 6B and 6C that the handle 84 is formed with a tongue 58 and handle 82 is formed with a groove 60 which is adapted for mating engagement to provide additional stability for device 10 when the handles 82 and 84 are juxtaposed.

Figure 7:
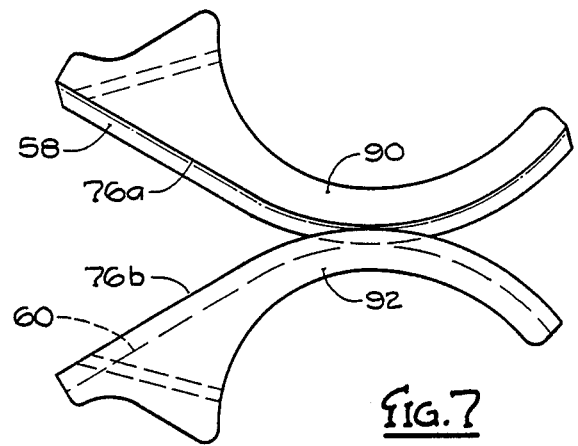
FIG. 7 is a top view of another embodiment of the handles of the device.

FIG. 7 shows another embodiment of the present invention in which the edge of handle 90 and edge of handle 92 are formed as arcuate surfaces 76a and 76b. This particular embodiment may be provided with either a tongue 58 and groove 60, as shown in FIG. 7, or could be joined together, as will be easily understood by the skilled artisan, with a series of protuberances 68 and their mating indentations 66.

Figure 8A:
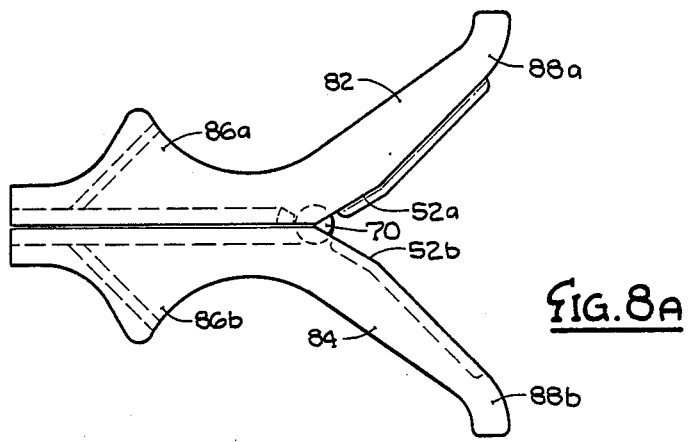
FIG. 8A is a top view of still another embodiment of the device.
Figure 8B:
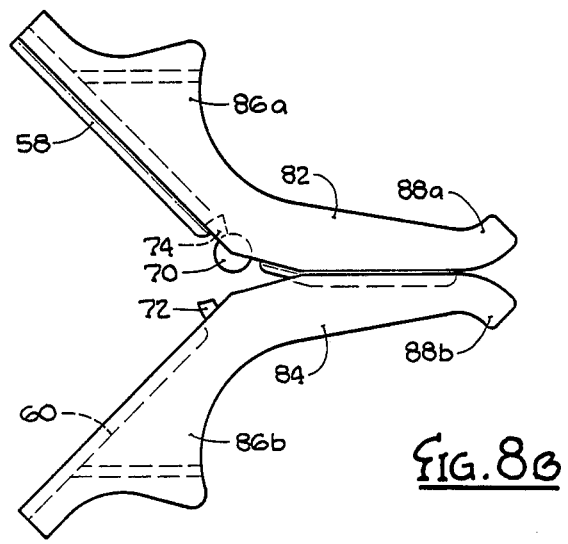
FIG. 8B is a top view of the device shown in FIG. 8A in its second stage of separation.

In yet another embodiment, the device 10 may have a single hinge 70 configuration rather than the double hinge shown in FIGS. 6A, 6B and 6C. Such a configuration is shown in FIGS. 8A and 8B. In its structure, hinge 70 comprises an arcuate finger 72 which is adapted to be received into an arcuate hollow 74. This junction of arcuate finger 72 with arcuate hollow 74 provides for bending and longitudinal stability of the handles when they are in a juxtaposed relationship. Further, it can be seen by comparing FIG. 6A with FIG. 6B that upon manipulation of the handles to separate the body portion 86a from the body portion 86b, hinge 70 is also separated.

Figure 9A:
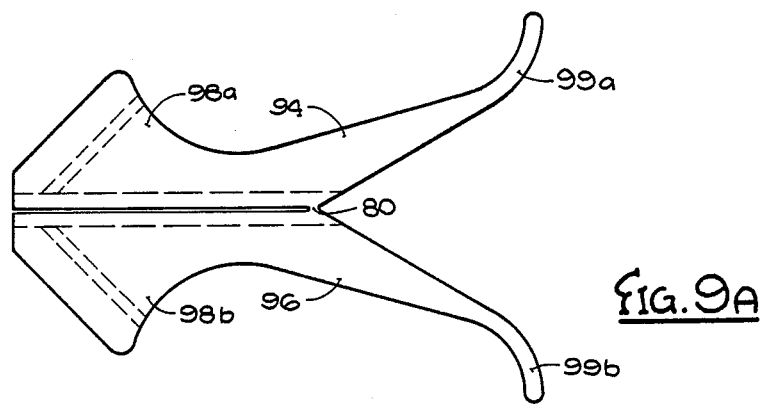
FIG. 9A is a top view of yet another embodiment of the device.
Figure 9B:
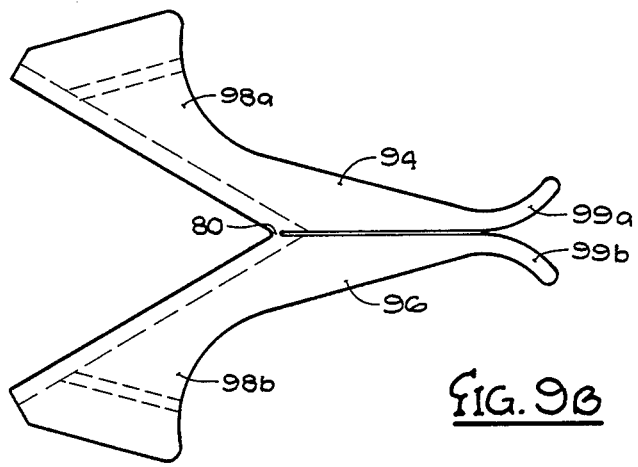
FIG. 9B is a top view of the embodiment of the device shown in FIG. 9A with the handles positioned for disengagement.

For the embodiments shown in FIGS. 3, 5, 6A, 6B and 6C, and 8A and 8B, extensions 50a and 50b are formed with intermediate flats 52a and 52b. This allows for a two stage operation of the device 10. It will be appreciated, however, that the intermediate flat 52a and 52b may be eliminated and instead a device 10, as shown in FIGS. 9A and 9B, may be presented wherein the handles 94 and 96 are formed without intermediate flats 52a and 52b. In this latter embodiment, a living hinge 80 may be formed which connects handle 94 with handle 96 at the juncture between their respective body portions 98a and 98b and their respective extensions 99a and 99b.

It will be understood in accordance with the present invention that the various embodiments for the handles are interchangeable as desired by the operator and that the handles may be employed with or without base member 12. Specifically, as envisioned for the present invention, a device 10 may incorporate any combination of desired hinges, stability structures, handle configurations and base members as herein disclosed.

OPERATION

Depending upon the particular medical procedure to be followed, use of the catheter placement device 10 of the present invention could include applications involving subcutaneous, intravenous, intraarterial, intramuscular, intraperitoneal and intrathecal placement of catheters. Device 10 could also be used to place a catheter through a vascular access port.

For the subcutaneous placement of catheters, the operation of catheter placement device 10 of the present invention is best appreciated by reference to FIGS. 6A, 6B and 6C. For subcutaneous procedures, placement of the device 10 is accomplished by first grasping the device 10 in one hand at the finger grips 62a and 62b. It is understood that the device 10 is symmetrical, thus allowing ambidextrous use. As such it can be grasped and manipulated by either the right or the left hand, depending upon the abilities and desires of the operator. When grasped at the finger grip 62a and 62b, additional rigidity for the device 10 may be provided by the operator.

Using the configuration for device 10 as shown in FIG. 6A, finger grips 62a and 62b are grasped and needle 18 is inserted under the skin of a patient. With the insertion of needle 18 into the patient, the catheter 20, which is carried in surrounding relation by the needle 18, will also be positioned as desired. The removal of needle 18 is accomplished in the following two-step operation. With needle 18 and catheter 20 in place, the operator grasps extensions 50a and 50b and squeezes them together in the direction of the arrows 43 as shown in FIG. 6B to bring the intermediate flats 52a and 52b into juxtaposition. As seen in FIG. 6B, this causes the respective ends 116 and 118 of handles 82 and 84 to be displaced and distanced one from the other. Consequently, body portion 48a separates from body portion 48b. This, in turn, causes separation of bifurcation 28a from 28b and begins the splitting of needle 18 into two parts, 18a and 18b, as shown in FIG. 6B.

Still referring to FIGS. 6A, 6B and 6C, it can be seen that whereas the juxtaposition of intermediate flats 52a and 52b cause a partial splitting of the needle 18, the operator can further manipulate the device 10 and bring the extension 50a and 50b into juxtaposition as shown in FIG. 6C. This manipulation, due to further squeezing handles 82 and 84 in the direction of arrows 43, will cause a further splitting of the needle 18 that results in a separation of the needle parts 18a and 18b. It should be appreciated that with the handles 82 and 84 in position, as shown in FIG. 6C, the needle 18 will have been completely withdrawn from the patient and be completely split. As shown in FIG. 6C, the base member 12 and the associated catheter 20 are left in place for further connection of the entry site 22 with medical solution containers or medical devices as may be required. At this point base member 12 may be slid along catheter 20 and attached to the body of the patient by the adhesive on undersurface 46 of base member 12. Additionally, catheter 20 may be secured by cleat 100 or looped under taping wing 30a or 30b for stability.

The actual mechanics of splitting of the needle can be best understood by reference back to FIGS. 4A and 4B. It will be recalled that as device 10 was put in place, bifurcation 28a and 28b were extended through the respective side openings 40a and 40b. Thus, upon squeezing the extensions 50a and 50b in the direction of arrows 43 to bring intermediate flats 52a and 52b into a side-by-side relationship, bifurcations 28a and 28b are respectively drawn through the side openings 40a and 40b. The interaction of abutments 44a and 44b with the bifurcations 28a and 28b assist in the splitting of the needle 18. Further, depending on the relative angle between handles 82 and 84 and base member 12, the bridge 42 which joins housing 36 to arch 32 will also assist in maintaining the positional relationship of the needle 18 and its bifurcations 28a and 28b with base member 12 as they are being drawn through the openings 40a and 40b. It can also be appreciated that the attachment of catheter 20 into channel 38 of housing 36 will provide for additional stability of the catheter during the operation of withdrawing needle 18 over the catheter 20. This action continues as device 10 is sequentially manipulated through the positions shown in FIGS. 6A, 6B and 6C.

The axial rigidity of catheter 20 is not challenged by the operation as described herein. Instead, the forces necessary to cause a splitting of the needle 18 are generated not by interaction against catheter 20 but by the action of handles 82 and 84, or 14 and 16, respectively, on the bifurcations 28a and 28b. Also, the forces on needle 18 generated by the abutments 44a and 44b of base member 12 stabilize the needle 18 and assist in splitting it. With this structure all of the forces necessary to split needle 18 take place at a distance from the insertion site and avoid trauma to the patient that would otherwise be caused by splitting the needle near the insertion site without such protection.

The intravenous placement of catheter 20 may be accomplished using an alternate embodiment of the device 10 in which there is no base member 12. In this embodiment, shown substantially in FIG. 5, a stylet 64 may provide additional rigidity to the catheter 20 during its placement within the hollow needle 18. Again, as with the other embodiments, the device 10 is grasped at the finger grips 62a and 62b for operation. As envisoned by the present invention, an extended length of catheter 20 may be initially positioned in the vein through use of device 10. Once the distal end 24 of hollow needle 18 is positioned within the vein, the catheter 20, which has been stiffened by stylet 64, can be fed further into the vein in accordance with the desires of the operator. Once the catheter 20 is in place, the hollow needle 18 is withdrawn from the patient. By virtue of the rigidity inparted to catheter 20 by the stylet 64, the catheter 20 will not be withdrawn. Instead, there will be a sliding withdrawal of the needle 18 over catheter 20. Once needle 18 is clear from the patient, the handles 14 and 16 may be squeezed together to split the needle 18. Stylet 64 is then removed and the catheter 20 left in place.

In this procedure, since needle 18 is completely withdrawn from the patient prior to being split and disjoined from catheter 20, base member 12 serves no purpose and can therefore be eliminated. As with the embodiment adapted for subcutaneous placement of a catheter 20, operation of this embodiment requires the manipulation of handles 14 and 16 to squeeze together the extensions 50a and 50b in the direction of arrows 43. As discussed above, this brings extensions 50a and 50b into a juxtaposed relationship thereby separating the respective body portions 48a and 48b of handles 14 and 16, or 82 and 84, to split needle 18 into its parts 18a and 18b. Again, as shown in FIGS. 6A, 6B and 6C, handles 82 and 84 may be formed with intermediate flats 52a and 52b to provide a two-stage manipulation of the handles to accomplish the separation.

It will also be understood by the skilled artisan that the handles as shown in FIGS. 8A and 8B in which a hinge is employed to provide relational stability between the handles 82 and 84 may be used in a manner similarly to that described here. Further, it should be understood that handles 94 and 96 formed substantially as shown in FIGS. 9A and 9B may be similarly employed.

While the particular articulated catheter placement device as herein shown and disclosed in detail is fully capable of obtaining the objects and providing the advantages as herein before stated, it is to be understood that it is merely illustrative of the presently preferred embodiment of the invention and that no limitations are intended to the details of construction or design herein shown other than as defined in the appended claims.

We claim:

1. A catheter placement device which comprises:
    a splittable hollow needle adapted to slidably receive a portion of said catheter therein and having a proximal end formed with a first bifurcation and a second bifurcation;
    a first handle having a body portion, a first end attached to said first bifurcation and a second end formed as an extension from said body portion;
    a second handle having a body portion, a first end attached to said second bifurcation and a second end formed as an extension from said body portion; and
    means to support said first and second handles for movment between an engaged position wherein said respective body portions are juxtaposed to present said respective extensions in a flared relationship, and a disengaged position wherein said respective extensions are juxtaposed to separate said first ends of said respective body portions into a flared relationship to distance said respective first ends and their attached bifurcations from each other to split said needle and disjoin said needle from said catheter.

2. A catheter placement device as recited in claim 1 wherein said support means comprises a hinge connecting said first handle with said second handle.

3. A catheter placement device as recited in claim 2 wherein said hinge integrally connects said first handle with said second handle.

4. A catheter placement device as recited in claim 1 further comprising:
    a base member formed with a housing having a channel therethrough for fixedly holding a portion of said catheter therein; and
    an arch set on said base member to hold the proximal end of said needle adjacent said bifurcations and longitudinally align said needle with said channel.

5. A catheter placement device as recited in claim 4 wherein said arch is spaced from said housing to form an opening through which said bifurcations are extended.

6. A catheter placement device as recited in claim 4 wherein said arch is spaced from said housing and said device further comprising:
    a bridge connecting said arch with said housing to form a first and a second side opening through which said first and said second bifurcations are respectively extended.

7. A catheter placement device as recited in claim 6 wherein said first handle and said second handle are formed with recesses for mating engagement with said housing when said handles are in the engaged position.

8. A catheter placement device as recited in claim 7 wherein said extensions are formed with flat surfaces for juxtaposed relationship therebetween.

9. A catheter placement device as recited in claim 1 wherein said first handle is formed with an intermediate flat between its said body portion and its said angled extension and said second handle is formed with an intermediate flat between its said body portion and its said angled extension to permit movement from said engaged position to a partially engaged position wherein said respective intermediate flats are juxtaposed while said respective body portions and said angled extensions are separated, and to further permit subsequent movement to said disengaged position.

10. A catheter placement device as recited in claim 9 wherein said support means comprises a hinge connecting said first handle with said second handle.

11. A catheter placement device as recited in claim 10 further comprising:
    a base member formed with a housing having a channel therethrough for fixedly holding a portion of said catheter therein; and
    an arch set on said base member to hold the proximal end of said needle adjacent said bifurcations and longitudinally align said needle with said channel.

12. A catheter placement device as recited in claim 11 wherein said arch is spaced from said housing to form an opening through which said bifurcations are extended.

13. A catheter placement device as recited in claim 12 wherein said arch is spaced from said housing and said device further comprises:
    a bridge connecting said arch with said housing to form a first and a second side opening through which said first and said second bifurcations are respectively extended.

14. A catheter placement device as recited in claim 13 wherein said first handle is formed with a tongue and said second handle is formed with a groove for mating engagement with said tongue of said first handle at the interface of juxtaposed portions of said first and second handles.

15. A catheter placement device as recited in claim 1 wherein said extensions are arcuate.

16. A catheter placement device comprising:

a splittable hollow needle for receiving a portion of said catheter therein, said needle having a pointed distal end and a proximal end divided to define a first bifurcation and a second bifurcation;

a pair of handles, each of said handles having a first end and a second end, said handles juxtaposed for touching engagement and moveable between a first position wherein said respective first ends are adjacent each other and said second ends are separated, and a second position wherein said first ends are spread into a flared relationship by urging together said second ends; and means to fixedly attach one of said bifurcations to said first end of one of said handles and to attach the other of said bifurcations to said first end of the other of said handles for spreading said bifurcations to split said needle and disjoin said needle from said catheter upon movement of said handles from said first position to said second position.

17. A catheter placement device as recited in claim 16 further comprising:

a base member formed with a housing having a channel therethrough with said needle disposed on said base to establish an extended passageway through said channel and said needle for receiving said catheter therein.

18. A catheter placement device as recited in claim 17 further comprising:

an arch set on said base member to hold the proximal end of said needle adjacent said bifurcations, said arch being spaced from said housing.

19. A catheter placement device as recited in claim 18 further comprising:

a bridge connecting said arch with said housing to form a first and a second side opening through which said bifurcations are respectively extended.

20. A catheter placement device as recited in claim 19 wherein one of said handles is formed with a groove and the other of said handles is formed with a tongue for mating engagement with said groove at the interface of juxtaposed portions of said handles.

21. A method for placing a catheter into a patient comprising the steps of:

A. Providing rigidity for said catheter with a device comprising: a splittable hollow needle adapted to slidably receive a portion of said catheter therein and having a proximal end divided to establish a first bifurcation and a second bifurcation; a first handle having a body portion, a first end attached to said first bifurcation and a second end formed as an extension from said body portion; a second handle having a body portion, a first end attached to said second bifurcation and a second end formed as an extension from said body portion; and means to support said first and second handles for movement between an engaged position wherein said respective body portions are juxtaposed to present said respective extensions in a flared relationship, and a disengaged position wherein said respective extensions are juxtaposed to separate said respective body portions into a flared relationship and distance said respective first ends and their attached bifurcations from each other to split said needle and disjoin said needle from said catheter;

B. Inserting said needles into said patient; and

C. Manipulating said device into said disengaged position.

* * * * *